United States Patent [19]
Kriesel

[11] Patent Number: 5,700,244
[45] Date of Patent: Dec. 23, 1997

[54] FLUID DISPENSER WITH FILL ADAPTER

[75] Inventor: Marshall S. Kriesel, Saint Paul, Minn.

[73] Assignee: Science Incorporated, Bloomington, Minn.

[21] Appl. No.: 577,496

[22] Filed: Dec. 22, 1995

Related U.S. Application Data

[63] Continuation-in-part of Ser. No. 192,031, Feb. 3, 1994, Pat. No. 5,484,415, which is a continuation-in-part of Ser. No. 156,685, Nov. 22, 1993, Pat. No. 5,433,709, which is a continuation-in-part of Ser. No. 53,723, Apr. 26, 1993, Pat. No. 5,354,278, which is a continuation-in-part of Ser. No. 870,521, Apr. 17, 1992, Pat. No. 5,263,940.

[51] Int. Cl.$^6$ ................................. A61M 37/00
[52] U.S. Cl. .................. 604/132; 604/131; 604/133
[58] Field of Search ....................... 604/131, 132, 604/133, 139, 142, 148, 153, 213, 218

[56] References Cited

U.S. PATENT DOCUMENTS

| | | | |
|---|---|---|---|
| 3,136,313 | 6/1964 | Enstrom et al. | 604/139 |
| 3,828,779 | 8/1974 | Ogle | 128/272 |
| 3,993,069 | 11/1976 | Buckles et al. | 604/132 |
| 4,180,070 | 12/1979 | Genese | 128/218 |
| 4,578,060 | 3/1986 | Huck et al. | 604/134 X |
| 4,883,483 | 11/1989 | Lindmayer | 604/411 |
| 4,886,495 | 12/1989 | Reynolds | 604/88 |
| 4,915,693 | 4/1990 | Hessel | 604/132 |
| 4,919,657 | 4/1990 | Haber et al. | 604/232 |
| 4,983,164 | 1/1991 | Hook et al. | 604/139 X |
| 5,011,477 | 4/1991 | Winchell et al. | 604/132 |
| 5,067,948 | 11/1991 | Haber et al. | 604/213 |
| 5,112,307 | 5/1992 | Haber et al. | 604/110 |
| 5,135,498 | 8/1992 | Kam et al. | 604/131 X |
| 5,137,511 | 8/1992 | Reynolds | 604/88 |
| 5,171,214 | 12/1992 | Kolber et al. | 604/82 |
| 5,304,165 | 4/1994 | Haber et al. | 604/411 |
| 5,334,162 | 8/1994 | Harris | 604/232 |
| 5,336,180 | 8/1994 | Kriesel et al. | 604/82 |
| 5,336,188 | 8/1994 | Kriesel | 604/132 |
| 5,364,386 | 11/1994 | Fukuoka et al. | 604/411 |
| 5,374,256 | 12/1994 | Kriesel | 604/232 |
| 5,397,303 | 3/1995 | Sancoff et al. | 604/82 |
| 5,411,480 | 5/1995 | Kriesel | 604/133 |
| 5,451,214 | 9/1995 | Hajishoreh | 604/235 |
| 5,454,793 | 10/1995 | Levander et al. | 604/235 |
| 5,462,535 | 10/1995 | Bonnichsen | 604/272 |
| 5,466,220 | 11/1995 | Brenneman | 604/87 |
| 5,472,422 | 12/1995 | Ljungquist | 604/89 |
| 5,484,406 | 1/1996 | Wong | 604/87 |

Primary Examiner—Sam Rimell
Attorney, Agent, or Firm—J. E. Brunton

[57] ABSTRACT

An elastomeric bladder stored energy type infusion apparatus which includes a unique fill assembly for use in controllably filling the fluid reservoir of the dispenser portion of the apparatus. The filling assembly includes a prefilled vial which is partially received within a novel adapter assembly that functions to operably couple the prefilled vial with the fluid dispenser subassembly of the apparatus. The body of the prefilled vial is surrounded by a protective covering until immediately prior to mating the assembly with the fluid delivery device.

15 Claims, 8 Drawing Sheets

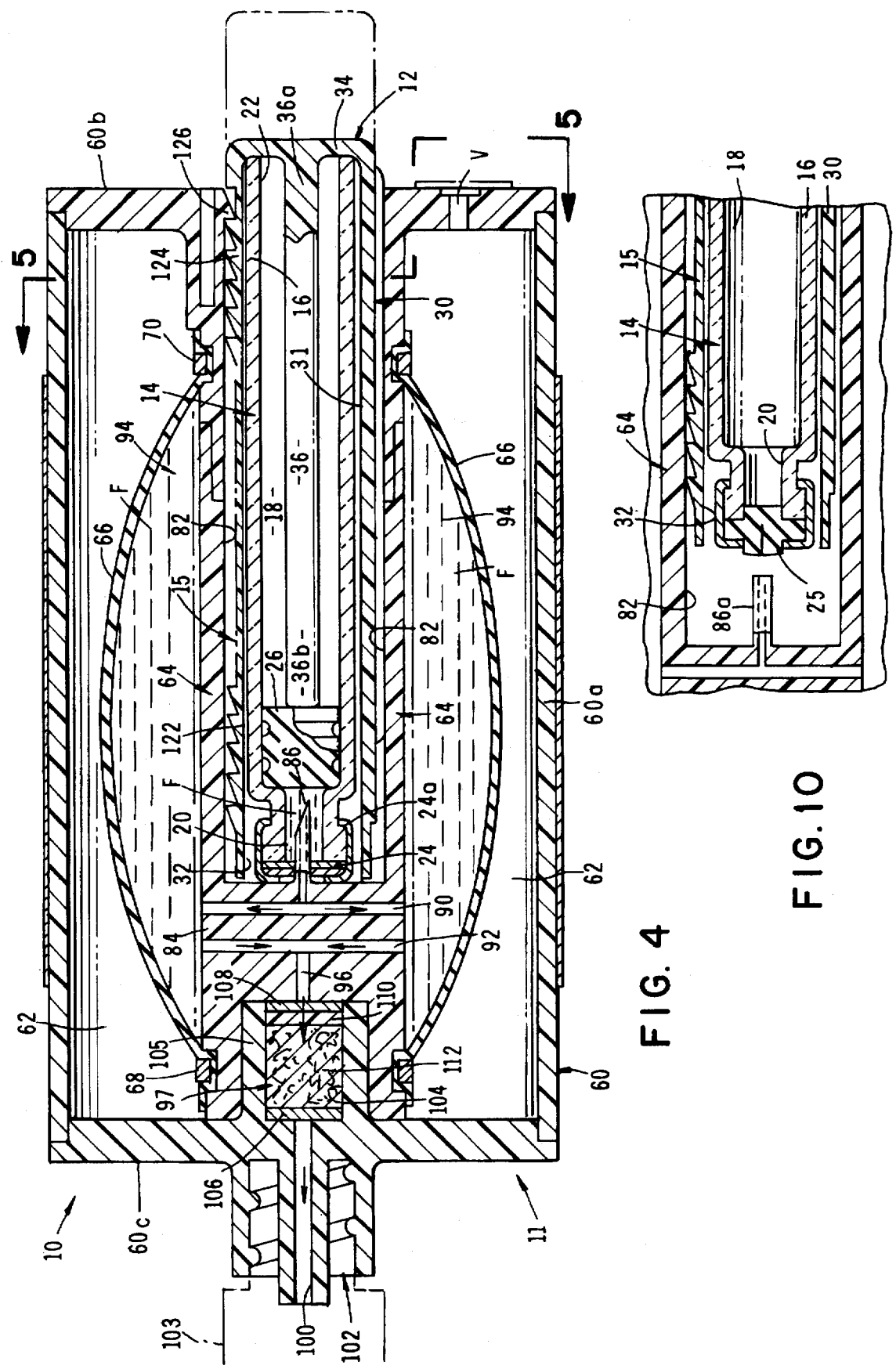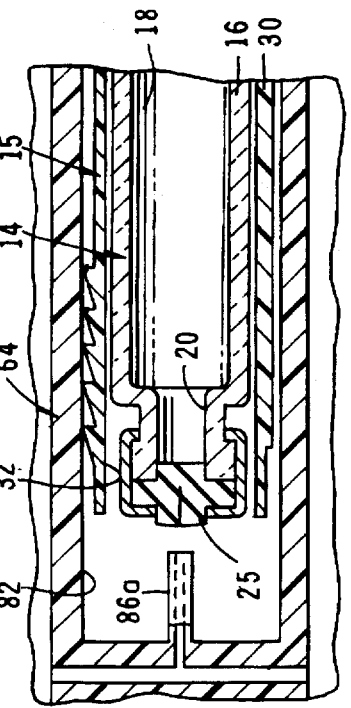
FIG. 4
FIG. 10

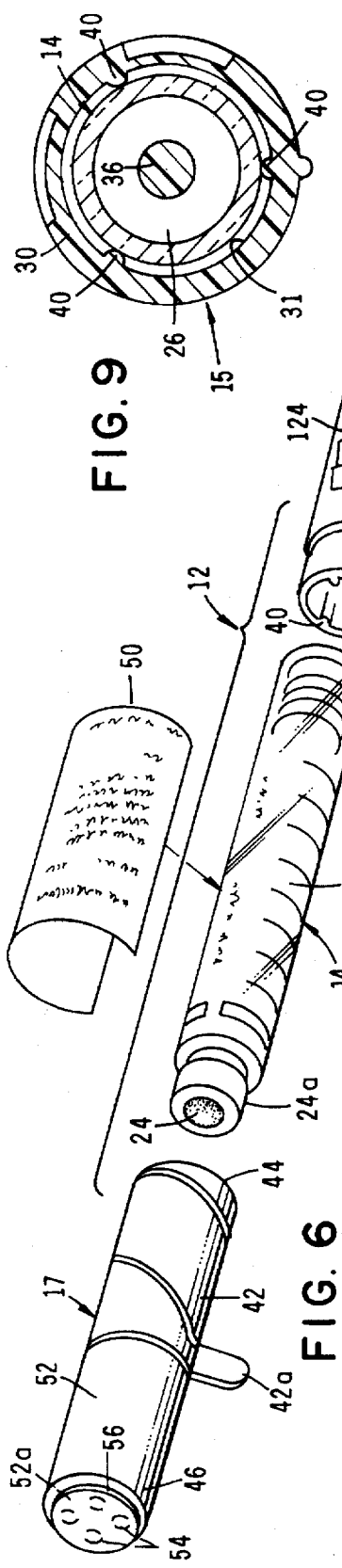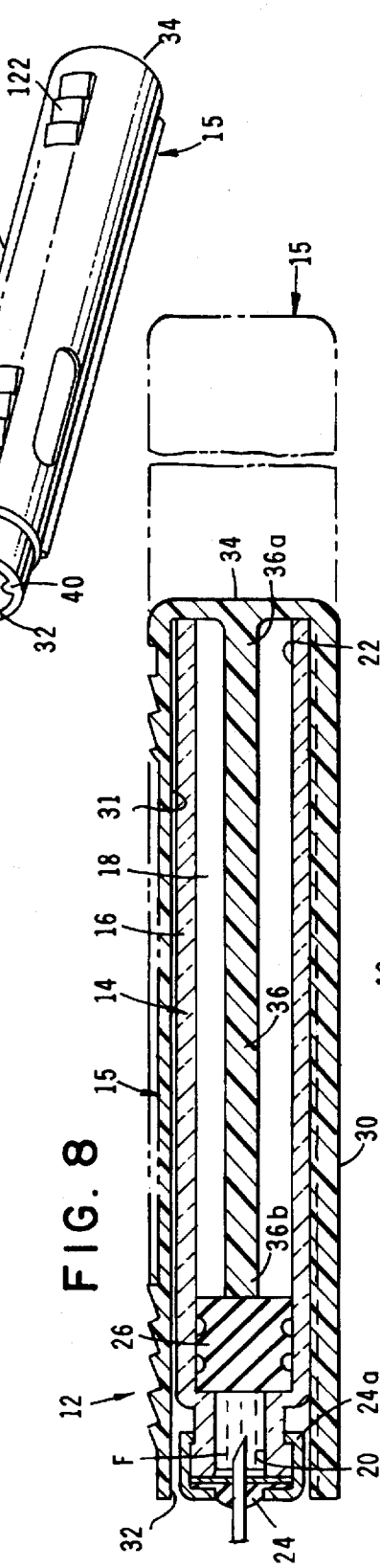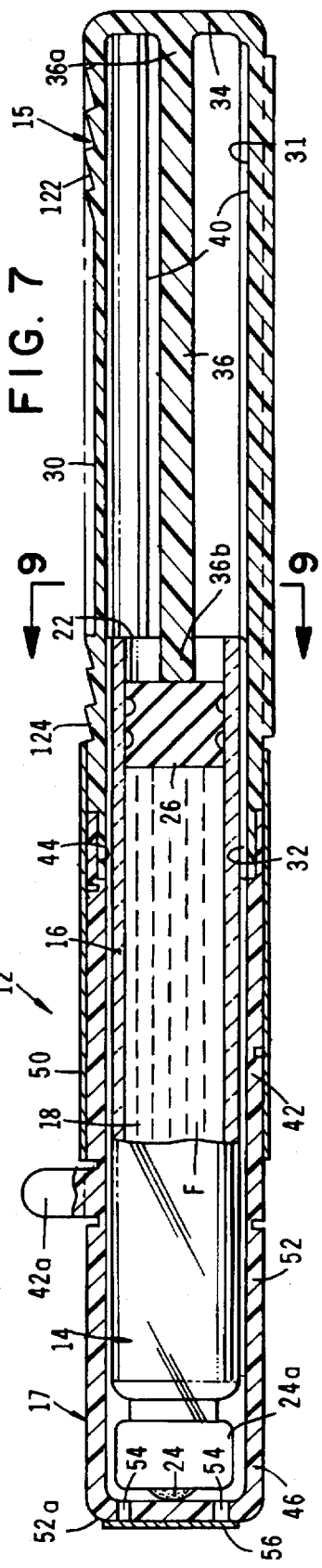

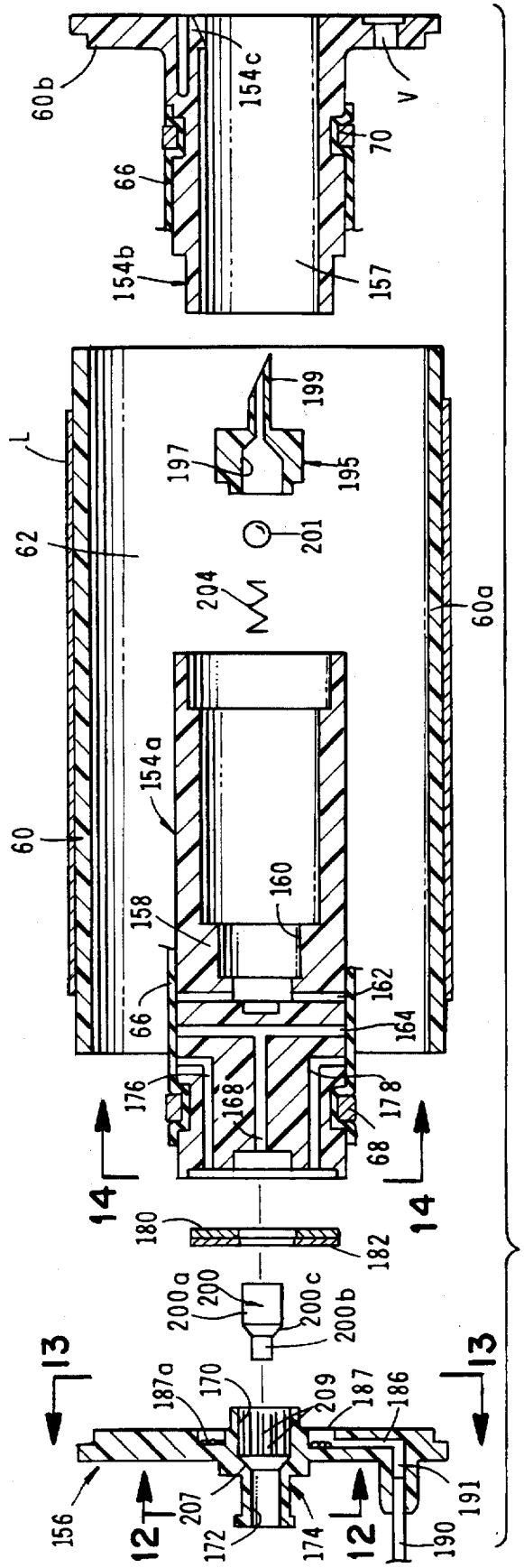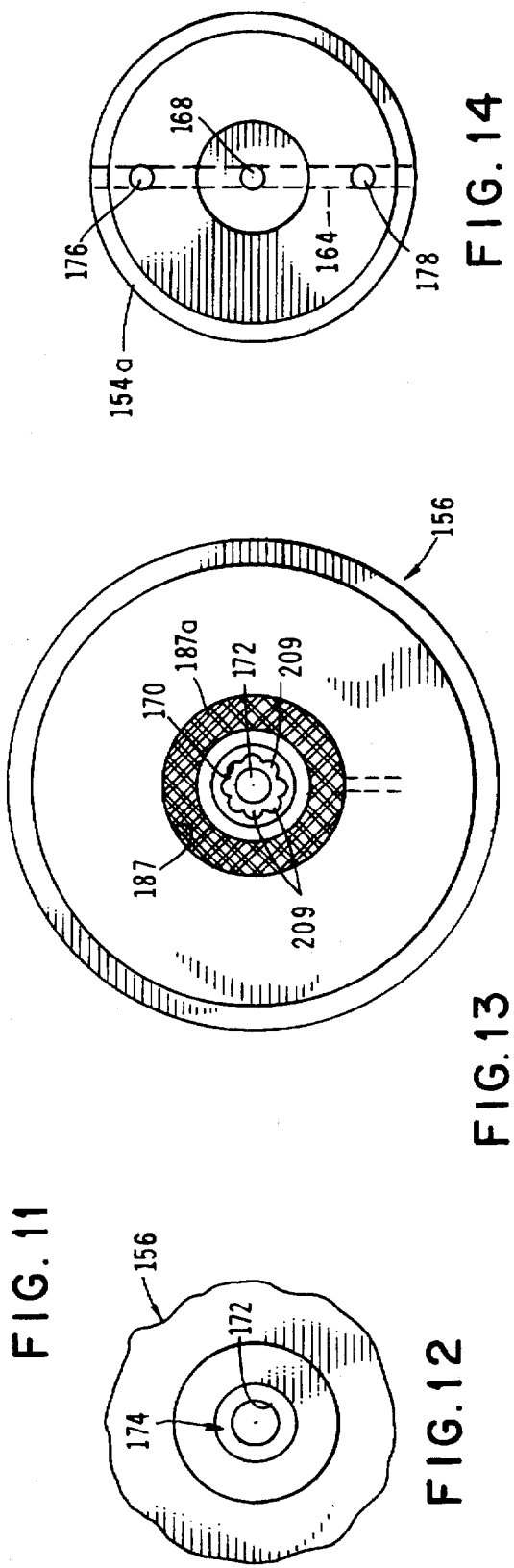
FIG. 11
FIG. 12
FIG. 13
FIG. 14

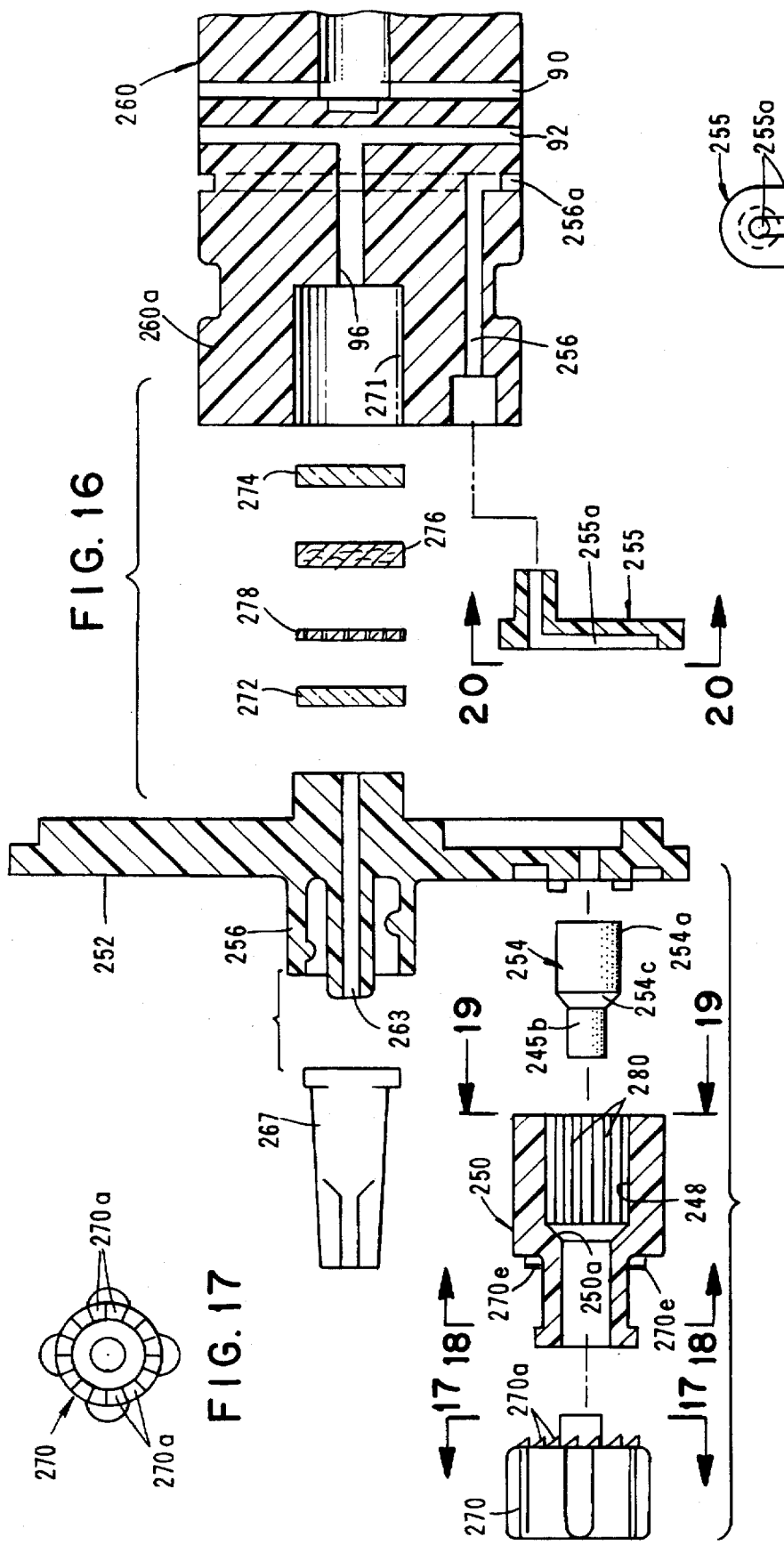

FLUID DISPENSER WITH FILL ADAPTER

BACKGROUND OF THE INVENTION

This is a Continuation-In-Part Application of U.S. application Ser. No. 08/192,031 filed on Feb. 3, 1994 entitled Fluid Dispensing Apparatus, now U.S. Pat. No. 5,484,415, which is a Continuation-In-Part of U.S. application Ser. No. 08/156,685 filed on Nov. 22, 1993 and has now issued into U.S. Pat. No. 5,433,709 entitled Fluid Dispenser; which is a Continuation-In-Part of Ser. No. 08/053,723 filed Apr. 26, 1993 and has now issued into U.S. Pat. No. 5,354,278; which is a Continuation-In-Part application of Ser. No. 07/870,521 filed on Apr. 17, 1992 and now issued into U.S. Pat. No. 5,263,940.

FIELD OF THE INVENTION

The present invention relates generally to infusion devices. More particularly, the invention concerns an elastomeric bladder type infusion apparatus which is used for delivering a beneficial agent to a patient at a substantially constant rate. The apparatus uniquely includes a fluid dispensing assembly and a novel fill assembly which can be interconnected with the dispensing assembly for filling the fluid reservoir thereof in the field prior to use.

DISCUSSION OF THE INVENTION

Many types of infusion pumps embodying an elastomeric balloon or bladder for delivery of a quantity of pharmaceutically active material to a patient have been suggested in the past. For example, U.S. Pat. No. 4,915,693 issued to Hessel discloses an infusion pump comprising an elastomeric bladder having at least an open end, and an elongate stress member extending concentrically within the entire length of the hollow portion of the bladder and having a fluid tight seal therewith. Both a filling port and an exit port are provided in the stress member, each in fluid communication with the interior of the bladder by way of an influent and an effluent lumen, respectively. The stress member has a diameter that is greater than the relaxed internal diameter of the bladder, and has a length that exceeds the relaxed internal length of the hollow portion of the bladder, so that it prestresses the bladder in both the axial and radial directions when disposed therein, substantially filling the bladder in its unfilled state. The Hessel device also includes a one-way valve on the stress member which permits flow in the influent lumen only in the direction of the interior of the bladder.

Another type of balloon type infusion device is disclosed in U.S. Pat. No. 4,386,929 issued to Perry, et al. The Perry, et al. device has spaced apart inlet and outlet means and the bladder which is capable of expanding and contracting radially and axially upon inflation and deflation. When deflated the lumen of the bladder is substantially completely filled by lumen filling means which protect the bladder from being punctured by the hypodermic needle used to fill and inflate the bladder. The lumen filling means resists the compressive load applied during insertion of the needle and maintains the inlet and outlet means in spaced apart relationship while providing substantially no resistance to the axial expansion of the bladder. By having the lumen of the bladder filled with the lumen filling means when the bladder is deflated, before its subsequent inflation and deflation, substantially complete expulsion of the fluid contents of the bladder can be obtained.

Very early balloon type infusion devices are described in U.S. Pat. Nos. 3,468,308 and 3,469,578 issued to Bierman. These patents disclose a device for expelling a liquid from a bladder member at an extremely slow rate over an extended period of time. In the device described in U.S. Pat. No. 3,469,578, the liquid is expelled solely by pressure induced on the liquid by the internal stresses of the distended bladder member. In the device disclosed in U.S. Pat. No. 3,468,308, the liquid is expelled by pressure control means which controls pressure applied to the exterior of the bladder member to control its rate of collapse.

In the devices described in both of the aforementioned patents, the bladder member comprises a balloon, or tube-like member which is typically distendable both lengthwise and laterally when initially pressured. Admission and discharge of liquid is of necessity, through a single neck, or outlet portion of the balloon-like bladder.

None of the prior art devices known to applicant include the unique fill assembly of the present invention which can be used to controllably fill the fluid reservoir of the fluid dispenser portion of the invention in the field. As will be better understood from the description which follows, the fill assembly of the present invention includes a fluid containing vial assembly mounted within a unique adapter assembly which functions to conveniently mate the vial assembly with the fluid dispenser portion of the apparatus to enable expeditious filling of the fluid reservoir thereof. Co-pending application, Ser. No. 08/192,031 describes in detail the construction of several types of elastomeric bladder stored energy type infusion devices of a character similar to the fluid dispenser portion of the apparatus described herein. The apparatus of the present invention comprises an improvement of these devices and accordingly application, Ser. No. 08/192,031, is hereby incorporated by reference in its entirety as though fully set forth herein.

SUMMARY OF THE INVENTION

It is an object of the present invention to provide an elastomeric bladder stored energy type infusion apparatus which includes a unique fill assembly for use in controllably filling the fluid reservoir of the dispenser portion of the apparatus.

Another object of the present invention is to provide an apparatus of the aforementioned character in which the fill assembly comprises a vial assembly of generally conventional construction that can be prefilled with a wide variety of medicinal fluids.

Another object of the present invention is to provide a fill assembly of the type described in the preceding paragraph in which the prefilled vial assembly is partially received within a novel adapter assembly that functions to operably couple the vial assembly with the fluid dispenser subassembly of the apparatus.

Another object of the invention is to provide an adapter assembly of the type described in which the body of the prefilled vial is surrounded by a protective covering until immediately prior to mating the assembly with the fluid delivery device.

Another object of the invention is to provide an apparatus as described in the preceding paragraphs in which the adapter assembly includes locking means for locking the assembly to the fluid delivery assembly following filling of the fluid reservoir thereof.

Another object of the invention is to provide a novel adapter assembly for use with the bladder type stored energy fluid dispenser subassembly of the apparatus which is easy to use, is inexpensive to manufacture, and one which maintains the prefilled vial in an aseptic condition until time of use.

Other objects of the invention are set forth in Ser. No. 08/192,031 which is incorporated herein by reference and in Ser. No. 08/053,723 which is, in turn, incorporated by reference in U.S. Ser. No. 08/192,031.

BRIEF DESCRIPTION OF THE DRAWINGS

FIG. 4 is an enlarged, cross-sectional view taken along lines 4—4 of FIG. 3.

FIG. 6 is a generally perspective, exploded view of one form of the fill assembly of the present invention.

FIG. 7 is an enlarged cross-sectional view of the fill assembly illustrated in FIG. 6 as it appears in an assembled configuration.

FIG. 8 is a cross-sectional view similar to FIG. 7, but showing the appearance of the component parts of the invention after the plunger of the container has been telescopically moved from a first to a second position.

FIG. 9 is an enlarged, cross-sectional view taken along lines 9—9 of FIG. 7.

FIG. 10 is an enlarged, cross-sectional view of the adapter subassembly receiving chamber of an alternate form of the apparatus which embodies a blunt cannula rather than a needle type cannula and showing the adapter subassembly partially inserted into the receiving chamber.

FIG. 11 is an exploded, cross-sectional view of an alternate form of the fluid dispenser assembly of the apparatus of the invention.

FIG. 12 is an enlarged view taken along lines 12—12 of FIG. 11.

FIG. 13 is an enlarged view taken along lines 13—13 of FIG. 11.

FIG. 14 is an enlarged view taken along lines 14—14 of FIG. 11.

FIG. 16 is an exploded, cross-sectional view of the forward portion of still another form of fluid dispenser assembly of the present invention.

FIG. 17 is a view taken along lines 17—17 of FIG. 16.

FIG. 18 is a view taken along lines 18—18 of FIG. 16.

FIG. 19 is a view taken along lines 19—19 of FIG. 16.

FIG. 20 is a view taken along lines 20—20 of FIG. 16.

DESCRIPTION OF ONE FORM OF THE INVENTION

Figure 1:
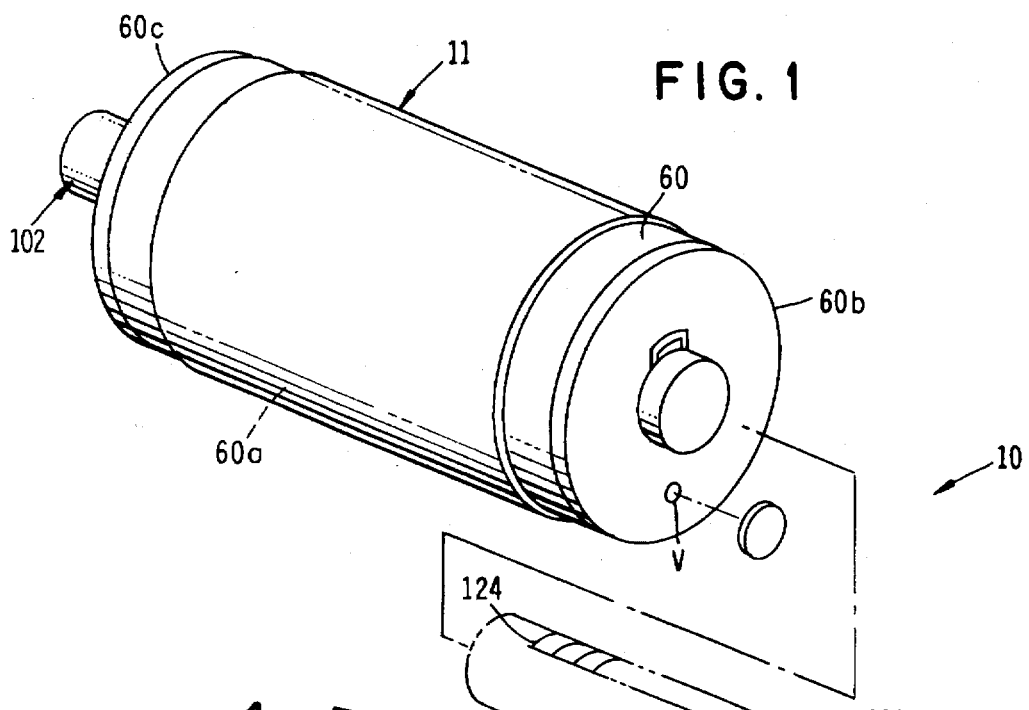
FIG. 1 is a generally perspective exploded view of one form of the fluid delivery apparatus of the present invention showing the fluid dispenser assembly and the fill assembly of the apparatus as they appear prior to mating the fill assembly with the dispenser assembly.
Figure 3:
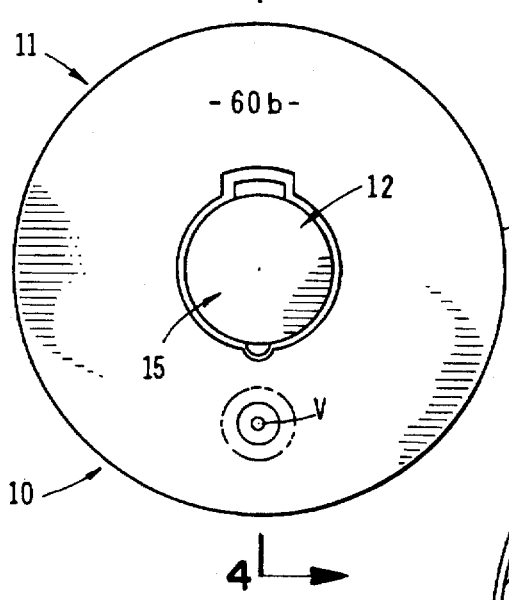
FIG. 3 is a right end view of the apparatus of FIG. 1.
Figure 5:
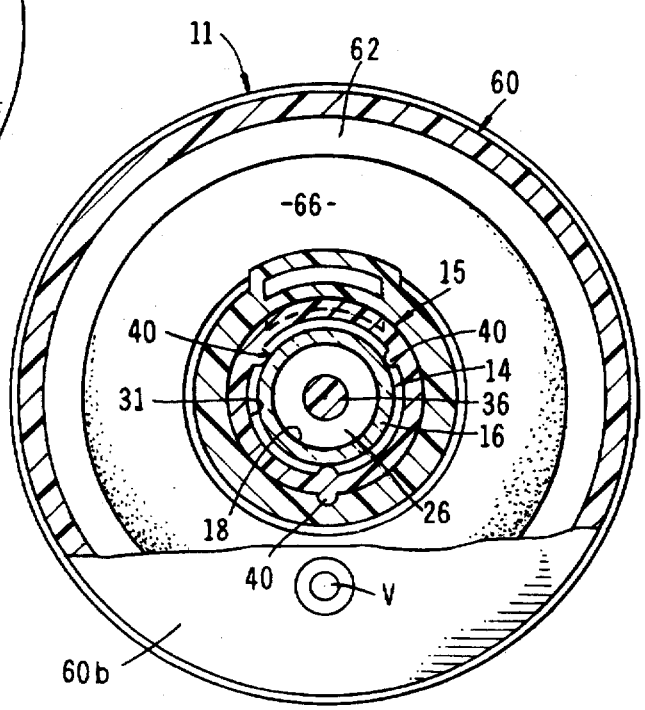
FIG. 5 is a view, partly in cross section, taken along lines 5—5 of FIG. 4.

Referring to the drawings and particularly to FIGS. 1 through 9, one form of the fluid dispenser apparatus of the present invention is there illustrated and generally identified by a numeral 10. Apparatus 10 comprises two main assemblies, namely a fluid dispensing assembly 11 and a fill assembly 12 for use in filling the fluid reservoir of the dispensing assembly. Dispensing assembly 11, the details of construction of which will presently be described, is similar in many respects to the dispenser described in Ser. No. 08/192,031 and includes a tubular support, a stored energy means for forming in conjunction with the support a fluid reservoir for containing medicinal fluids to be controllably infused into a patient and a generally cylindrically shaped housing which circumscribes the tubular support and stored energy means.

Figure 2:
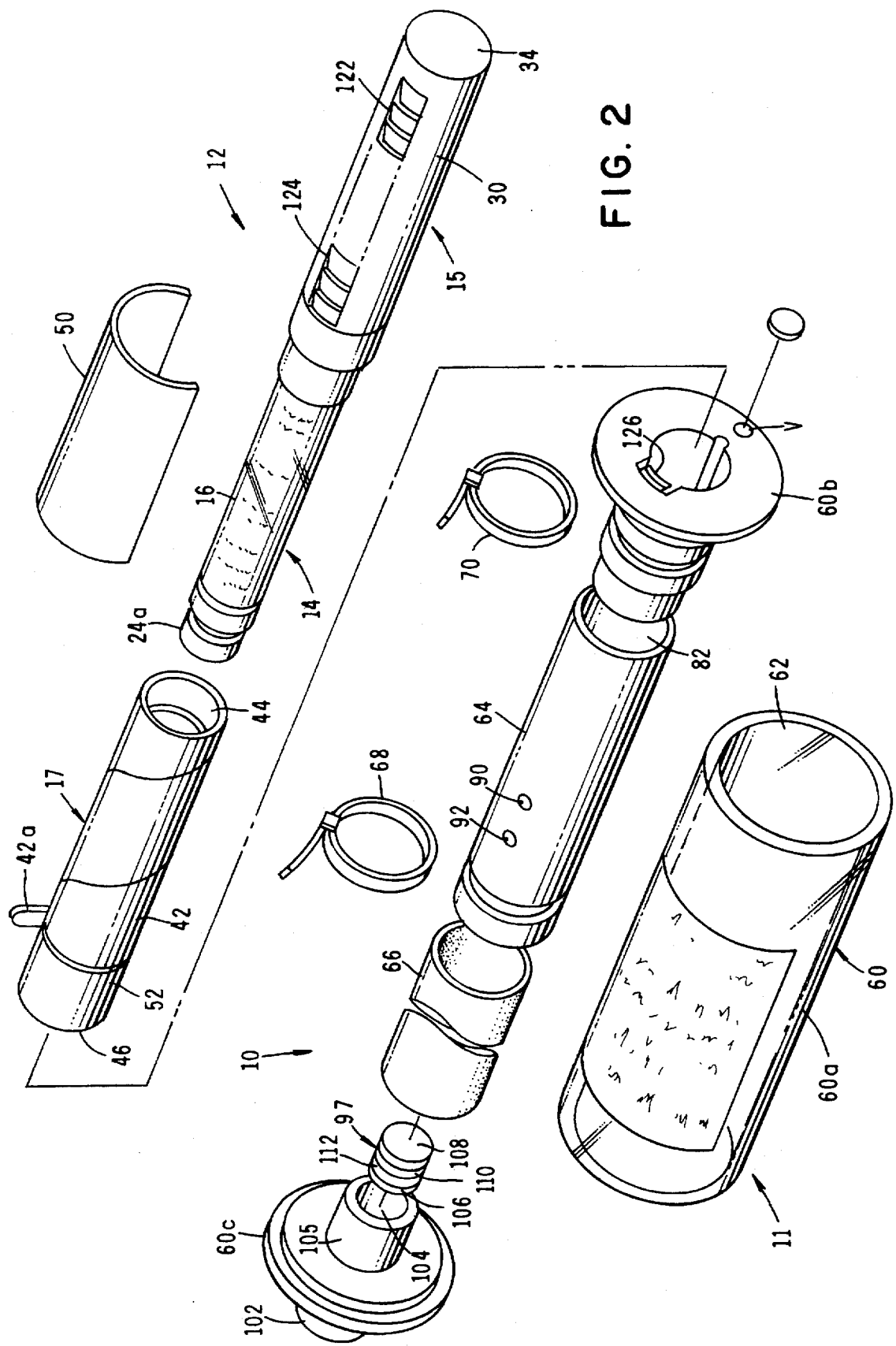
FIG. 2 is a generally perspective, exploded view of the apparatus shown in FIG. 1.

As best seen by referring to FIGS. 2 and 6, the fill assembly portion 12 of the apparatus comprises a container subassembly 14, an adapter subassembly 15, and a cover subassembly 17, the character of which will presently be described. Container subassembly 14 includes a body portion 16, having a fluid chamber 18 for containing an injectable fluid "F" provided with first and second open ends 20 and 22 (FIGS. 7 and 8). First open end 20 is sealably closed by closure means here provided in the form of a pierceable septum assembly 24. Septum assemby 24 is held securely in position by clamping ring 24a. As best seen in FIGS. 7 and 8, a plunger 26 is telescopically movable within chamber 18 of container subassembly 14 from a first location shown in FIG. 7 where it is proximate first open end 22 to a second position shown in FIG. 8 where it is proximate first open end 20. The vial portion of the container subassembly 14 can be constructed of various materials such as glass and plastic.

Referring particularly to FIG. 6, it can be seen that the adapter subassembly 15 comprises a hollow housing 30 having a first open end 32 and a second closed end 34 (FIG. 8). Container subassembly 14 is telescopically receivable within open end 32 of housing 30 in the manner shown in FIG. 7 so that the housing can be moved from the first extended position shown in FIG. 7 to the vial encapsulation position shown in FIG. 8. Forming an important part of the adapter subassembly is pusher means shown here as an elongated pusher rod 36 which functions to move plunger 26 within fluid chamber 18 from the first position shown in FIG. 7 to the second position shown in FIG. 8. In the form of the invention shown in the drawings, pusher rod 36 has a first end 36a interconnected with closure wall 34 and an opposite end 36b which engages plunger 26 and causes telescopic movement of the plunger within chamber 18 of container subassembly 14 as housing 30 is moved from the extended position into the vial encapsulating position shown in FIG. 8.

As best seen by referring to FIG. 9, the interior wall 31 of housing 30 is provided with circumferentially spaced-apart protuberances 40 which engage and center container subassembly 14 within housing 30. Due to the small surface area presented by protuberances 40, there is little frictional resistance to the sliding movement of container subassembly 14 relative to housing 30 as the housing is moved from the extended position shown in FIG. 7 into the vial encapsulating position shown in FIG. 8.

Referring to FIG. 6, it is to be noted that cover subassembly 17 of the fill assembly of the present form of the invention includes a spiral wound, frangible portion 42 having a first open end 44 for telescopically receiving body portion 16 of container subassembly 14 (FIG. 7) and a second closed end 46. Portion 42 initially circumscribes a major portion of container subassembly 14 in the manner best seen in FIG. 7. An integral pull tab 42a is provided to permit the spiral wound, frangible portion to be pulled from container subassembly 14 so as to expose a substantial portion of body 16. As best seen in FIG. 6, a medicament label 50 circumscribes spiral wound portion 42 and serves to prevent accidental unwinding of the spiral portion from the container subassembly 14. However, upon pulling tab 42a, the spiral portion will unwind and, in so doing, will tear medicament label 50 so that the spiral portion 42 of the covering as well as the cylindrical portion 52 which, also comprises a part of the cover assembly, can be slipped from the container 14 so as to expose to view septum assembly 24.

As shown in FIGS. 6 and 7, apertured end 52a of cylindrical portion 52 of subassembly 17 is provided with venting apertures 54 which are covered by a porous vent patch 56 which can be constructed from any suitable porous material that will permit air entrapped within the interior of subassembly cover subassembly 17 to be expelled to atmosphere as the subassembly is placed over container subassembly 14.

Turning once again to FIGS. 2 through 5, the fluid dispensing assembly 11 of the apparatus of the invention can be seen to comprise an elongated housing 60 having an internal chamber 62 and a support 64 disposed within internal chamber 62 and extending longitudinally thereof. The stored energy means of the invention is here provided in the form of a generally cylindrically shaped, elongated elastomeric member 66. Housing 60 includes a generally cylindrically shaped central portion 60a and inlet and outlet end plates 60b and 60c respectively. Central section 60a and end plates 60b and 60c may be constructed from any suitable rigid plastic material such as a polycarbonate and the end plates can be affixed to the central section by any suitable means such as adhesive bonding or an appropriate sonic weldment. Elastomeric member 66 is securely affixed proximate its ends to a two-part support 64 (FIG. 4) by means of suitable ring clamps 68 and 70 such as self-locking plastic panduit strips of the character shown in FIG. 2.

As best seen by referring to FIG. 4, support 64 is provided with an elongated receiving chamber 82 having an inner end wall portion 84 with supports a hollow piercing cannula 86 which extends into receiving chamber 82. Wall 84 is provided with first and second radially extending fluid passageways 90 and 92. Passageway 90 communicates proximate its central portion with the fluid passageway of hollow cannula 86 and communicates at its extremities with a fluid reservoir 94 formed between elastomeric member 66 and the outer central surface of support 64. The extremities of passageway 92 also communicate with fluid reservoir 94, while the center of the passageway communicates with a longitudinally extending outlet passageway 96, which, in turn, communicates with flow control means 97, the character of which will presently be described. End plate 60c is provided with an outlet passageway 100 which is in communication with the flow control means 97 and forms a part of luer connector like construction 102 which is integrally formed with end plate 60c.

The novel flow control means of the form of the invention shown in FIG. 4 comprises an assemblage made up of three disc-like wafers which are mounted proximate the ends of a rate control chamber 104 formed in a cylindrical extension 105 of the end plate 60c. Wafers 106 and 108 of the assemblage comprise porous glass distribution frits of a character well known in the art, while intermediate wafer 110 comprises a filter member. A rate control assemblage, generally designated by the numeral 112, is disposed between glass frit 106 and filter member 110.

Filter member 110 can be constructed from a wide variety of materials, but a material comprising polysulfone sold by Gelman Sciences under the name and style of SUPOR has proven satisfactory for the purpose. Rate control assemblage 112 is preferably constructed from a porous material having small flow apertures which controllably impede fluid flow. However, a number of other materials can also be used to construct this permeable member including metals, ceramics, cermet, plastics and glass. The rate control member can be specifically tailored to accommodate very specific very specific delivery regimes including very low flow and intermediate flow conditions. Such rate control assemblages are well known by those skilled in the art.

In using the apparatus of the invention, with the fill assembly in the filled configuration shown in FIG. 7, the cover subassembly is first removed from the container subassembly by pulling on pull-tab 42a. This will cause the spiral portion 42 of the cover subassembly to tear away from the container subassembly so that it can be separated from the forwardly disposed portion 52. Once the spiral wound portion 42 is removed, cylindrical portion 52 can also be removed and discarded. Removal of the cover subassembly exposes the forward portion of the container subassembly and readies the adapter subassembly for interconnection with the fluid dispensing assembly 11.

Mating of the adapter subassembly 15 with the dispensing assembly 11 is accomplished by telescopically inserting the exposed container portion of the container subassembly 14 into receiving chamber 82 and pushing the assemblage forwardly of housing 60. As the adapter subassembly approaches a seated position within receiving chamber 82, the piercing cannula 86 connected to end portion 64 will pierce septum assembly 24 of the container subassembly. Once the fluid flow path between the hollow cannula and the fluid reservoir 94 of the fluid dispensing device is thus created via passageway 90, a continued inward movement of the adapter subassembly 15 will cause pusher rod 36 thereof to move plunger 26 forwardly of chamber 18 to a position shown in FIG. 4. As plunger 26 is moved forwardly of chamber 18, fluid contained within the chamber will flow through the hollow cannula into passageway 90 of partition wall 84 and then into fluid reservoir 94. As the fluid under pressure flows into reservoir 82, membrane 66 will be distended outwardly in the manner shown in FIG. 4 wherein the central portion thereof is spaced from support 64. Rings 68 and 70, which are in clamping engagement with support 64 function to seal the membrane against the end portions of the support and prevent leakage of fluid between the membrane and the support. As the distendable membrane expands outwardly, the displaced air within housing 60 will be vented to atmosphere via vent means "V" provided in end plate 60b.

It is to be understood that membrane 66 can comprise a single film layer or can be made up of a laminate construction comprising of a number of cooperating layers of material. Materials suitable for constructing membrane 66 include latex rubber, polyisoprene (natural rubber), butyl rubber, nitrile rubber, other homopolymer, copolymers (random, alternating, block, graft, crosslink and starblock), mechanical poly blends and interpenetrating polymer networks.

Once distendable membrane 66 is distended to form fluid reservoir 94, the apparatus will remain in this filled condition until outlet passageway 100 of the luer like connector assembly 102 is opened by the removal of a suitable closure cap 103 of the character shown by the phantom lines in FIG. 4. With outlet passageway 100 opened, the stored energy means or membrane 66 will tend to return to a less distended condition causing fluid to flow outwardly of the apparatus via passageway 92, passageway 96, through the flow control means 97, and then through passageway 100.

Materials suitable for use in constructing housing 60 and support 64 include metals, rubber or plastics that are compatible with the liquids they contact and are preferably non-allergenic type material. Examples of such materials are: stainless steel, aluminum, latex rubber, butyl rubber, nitrile rubber, polyisiprene, styrene-butadiene copolymer, silicones, polyolefins such as polypropylene and polyethylene, polyesters, polyurethane, polyamides and polycarbonates. Manufactures of suitable materials for use in constructing the fluid dispensing assembly of the invention include: Dow Corning of Midland, Mich.; General Electric of Schenectady, N.Y.; and Shell Chemical Company of Houston, Tex.; DuPont Chemical of Wilmington, Del.; and Eastman Chemical of Kingsport, Tenn.

In order to securely lock the adapter subassembly with the dispensing assembly 11 after the reservoir has been filled, novel locking means are provided. The locking means here comprise a series of locking teeth 122 and 124 respectively. As indicated in FIG. 4, these locking teeth are constructed so that they will slide under a flexible locking tab 126, which is provided proximate the entrance of receiving chamber 82, as the adapter subassembly is urged inwardly of receiving chamber 82. However, once the adapter subassembly has reached the fully forward position shown in FIG. 4, locking tab 126 will engage one of the teeth 124 and effectively prevent removal of housing 60 of the adapter subassembly from passageway 82. With this novel construction, once the reservoir 94 has been filled with the fluid "F" contained in the container subassembly, the adapter assembly cannot be removed from the fluid dispensing device and, thereby preventing system adulteration.

Turning to FIG. 10 another form of the apparatus of the invention is there shown. This apparatus is similar in construction and operation to that shown in FIG. 1 through 9 save that the septum of container septum assembly, designated in FIG. 10 as 25, is a slit septum and the cannula, designated in FIG. 10 as 86a, is a blunt cannula configuration. Such constructions are well known to those skilled in the art and can be used in lieu of conventional non-coring pierceable septums and sharp needles. The blunt cannula type device partially shown in FIG. 10 operates in the same manner as the apparatus of FIGS. 1 through 9.

Referring next to FIGS. 11 through 15, still another embodiment of the present invention is there illustrated. This embodiment is also similar in many respects to the embodiment shown in FIGS. 1 through 9 and, accordingly, like numbers have been used to identify like components. The primary difference between this latest form of the invention and that previously described herein is the provision of an alternate fill means for filling the reservoir of the device. Forming a part of this novel alternate fill means are strategically located valve means which are disposed within the dispensing assembly for controlling fluid flow through the apparatus. As will become apparent from the discussion that follows, this novel valve means permits the inclusion of a fill line 211, which forms a part of the alternate fill means, and a fluid delivery line each of which communicates with the reservoir of the device.

Figure 15:
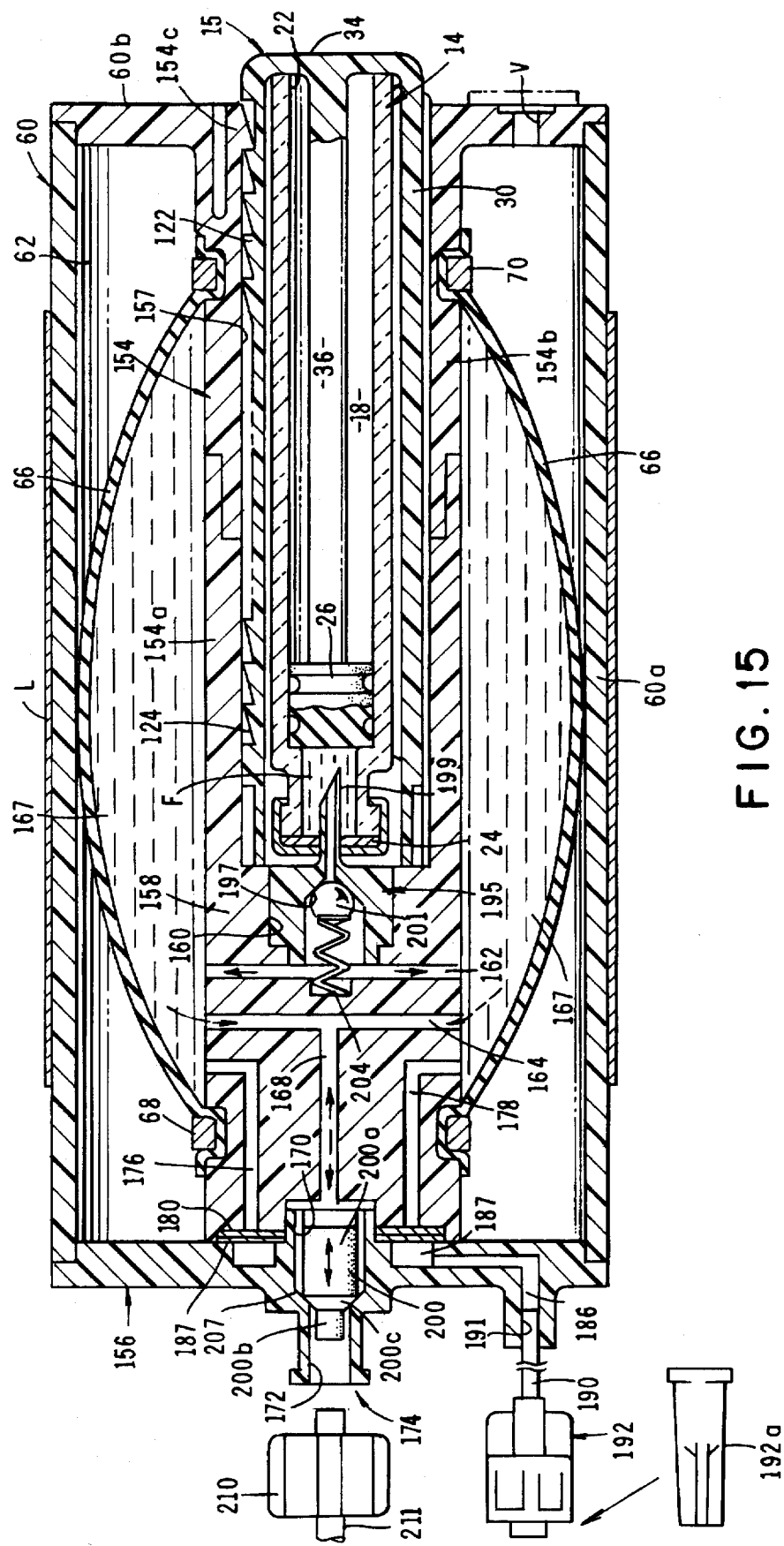
FIG. 15 is an enlarged, cross-sectional view of the fully assembled dispenser portion of the apparatus shown in FIG. 11 operably coupled with the fill assembly of the apparatus of the invention.

Considering particularly FIGS. 11 and 15, the fluid dispensing assembly of this latest form of the invention can be seen to comprise an elongated housing 60 having an internal chamber 62 and a two-part support 154 disposed within internal chamber 62 and extending longitudinally thereof. The stored energy means of the invention is here provided in the form of a generally cylindrically shaped, elongated elastomeric member 66 of identical construction to that previously described.

Housing 60 comprises a cylindrically shaped central portion 60a and inlet and outlet end plates 60b and 156 respectively. Central section 60a and end plates 60b and 156 may be constructed from any suitable rigid plastic material such as a polycarbonate and the end plates can be affixed to the central section by any suitable means such as adhesive bonding or an appropriate sonic weldment. As before, end plate 60b is provided with a vent port "V" for venting gases within the housing to atmosphere. Elastomeric member 66 is securely affixed proximate its ends to support 154 by means of suitable ring clamps 68 and 70 such as self-locking plastic panduit strips.

As best seen by referring to FIG. 15, support 154 is formed by a forward section 154a and a rearward section 154b which is integrally formed with end plate 60b. Support 154 is provided with an elongated receiving chamber 157 having an inner end wall portion 158 which is provided with a central counterbore 160 (FIG. 11). Wall 158 is also provided with first and second radially extending fluid passageways 162 and 164. Passageway 162 communicates proximate its central portion with counterbore 160 and communicates at its end portions with a fluid reservoir 167 (FIG. 15) formed between elastomeric member 66 and the outer central surface of support 154. The extremities of passageway 164 communicate with fluid reservoir 167 while the center portion thereof communicates with an inlet passageway 168, which, in turn, communicates with a central bore 170 provided in end plate 156. End plate 156 is also provided with an inlet passageway 172 which forms a part of a luer like connector 174 which is integrally formed with end plate 156.

As shown in FIG. 15, end wall or partition 158 of support 154 is also provided with a pair of radially spaced, longitudinally extending fluid passageways 176 and 178. The inboard end of each of these passageways communicates with reservoir 167 while the outboard ends thereof communicate with novel flow control means for controlling fluid flow outwardly of passageways 176. This flow control means here comprises an annular shaped filter 180 and an annular shaped rate control member 182. Member 182 overlays a generally annular shaped chamber 187 formed in end plate 156, which chamber, in a manner presently to be described, communicates with the fluid outlet port of the apparatus via bore 191. As best seen in FIG. 13, annular chamber 187 includes a multiplicity of microchannels and grooves 187a which direct the flow of fluid toward an outlet passageway 186 formed in end plate 156 (see also FIG. 11). Outlet passageway 186 communicates with a fluid delivery tube 190 one end of which is received within a bore 191 formed in end plate 156. The opposite end of tube 190 is connected to a conventional luer fitting 192. A female luer cap 192a (FIG. 15) is mateable with fitting 192 to block fluid flow outwardly of delivery tube 190.

Forming an important aspect of this latest form of the dispensing device is the provision of a first check valve means for controlling fluid flow toward inlet passageway 162. This first valve means is here provided in the form of a first valve assembly which includes a valve seat defining housing 195 which has an internal valve seat 197 and an outwardly extending hollow piercing cannula 199 (FIG. 11). Housing 195, which is closely receivable within counterbore 160 formed in wall 158, houses a generally spherical shaped rubber or silicone valve member 201 which is normally held in sealing engagement with a seat 197 formed in housing 195 by a biasing means shown here as a coil spring 204.

A second check valve means controls fluid flow between passageway 172 and passageway 168. This second valve means which forms a part of the alternate fill means, comprises a valve member 200 which includes a body portion 200a, a neck portion 200b and an intermediate tapered shoulder 200c. Check valve member 200 can be constructed from rubber, silicone, urethane and like materials. When reservoir 167 is filled, fluid under pressure within passageway 168 will maintain shoulder 200c of the valve member in sealing engagement with the valve seat 207 formed in end plate 156.

When the alternate fill means is used to fill reservoir 167 of the dispensing portion of the apparatus, a filling line assembly 210, which includes a fill line 211, is connected to luer like connector 174 so that fluid under pressure can be introduced into passageway 172. This fluid under pressure will move valve 200 member inwardly causing shoulder 200c to move away from seat 207 thereby permitting fluid to flow past valve member body 200a, through a plurality of circumferentially spaced channels 209 formed in end plate 156 (see FIGS. 11 and 13). Fluid will then flow into inlet passageway 168 to passageway 164 to either fill or partially fill the reservoir 167. By way of example a dilluent could be introduced into reservoir 167 via the filling line assembly 210 and an injectable drug could be introduced into the reservoir using fill assembly 12.

When it is desired to fill or partially fill reservoir 167 with the fill assembly of the invention, the cover subassembly is, as before, removed from the container subassembly by pulling on pull-tab 42a and the adapter subassembly is then telescopically inserted into receiving chamber 157 in the manner shown in FIG. 15.

As the adapter subassembly approaches a seated position within the receiving chamber 157, the piercing cannula 199 will pierce septum 24 of the container subassembly. Once a fluid flow path between the hollow cannula and the fluid reservoir 167 of the fluid dispensing device is thus created, a continued inward movement of the adapter subassembly 15 will cause pusher rod 36 thereof to move plunger 26 forwardly of chamber 18 to a position shown in FIG. 15. As plunger 26 is moved forwardly of chamber 18, fluid contained within the chamber will flow through the hollow cannula and will move valve element 201 away from seat 197 against the urging of spring 204. With the valve means open, the fluid will flow into passageway 162 of partition wall 158 and then into fluid reservoir 167. As the fluid under pressure flows into reservoir 167, membrane 66 will be distended outwardly in the manner shown in FIG. 15 wherein the central portion thereof is spaced from support 154. It is to be noted that at the commencement of the fluid delivery step, spring 204 will urge valve element 201 into sealing engagement with seat 197 thereby maintaining reservoir 167 in a filled condition.

As before, locking means, including a flexible locking tab 154c, is provided on support 154 to engage locking teeth 122 and 124 provided on adapter 15 in order to lock the adapter in position within housing 150 after the filling step has been completed. A medicament label "L" surrounds housing 150 to identify the medicament contained within the reservoir 167.

Once distendable membrane 66 is distended to form fluid reservoir 167, the apparatus will remain in this filled condition until the outlet passageway of the fitting 192 is opened by the removal of female luer 192a (FIG. 15). With the outlet passageway thus opened, the stored energy means or membrane 66 will tend to return to a less distended condition causing fluid to flow outwardly of the apparatus via passageway 176 and 178, through the flow control means 97, into annular chamber 187, and then outwardly through passageway 186 and into delivery tube 190.

Figure 21:
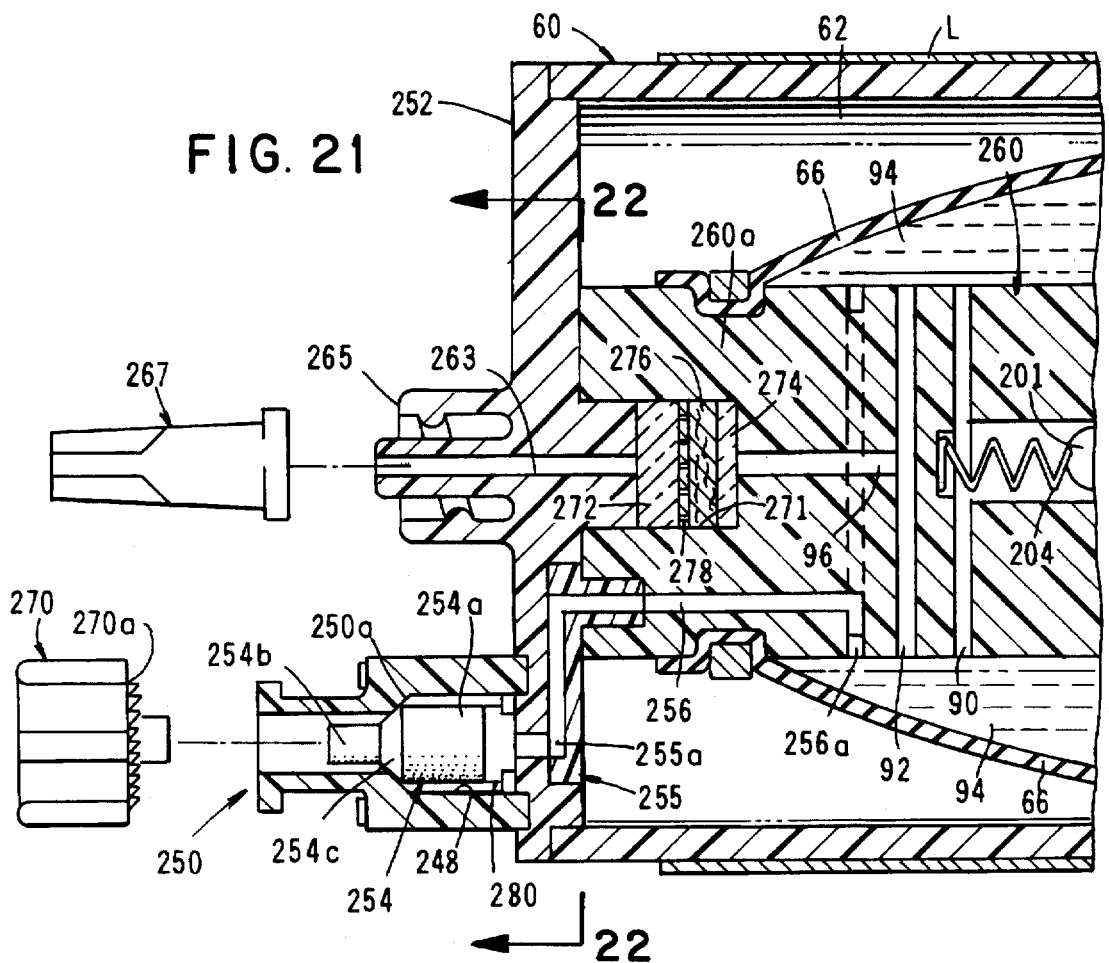
FIG. 21 is a cross-sectional view of the forward portion of the fluid delivery assembly shown in FIG. 16 as it appears with the various components thereof assembled together.
Figure 22:
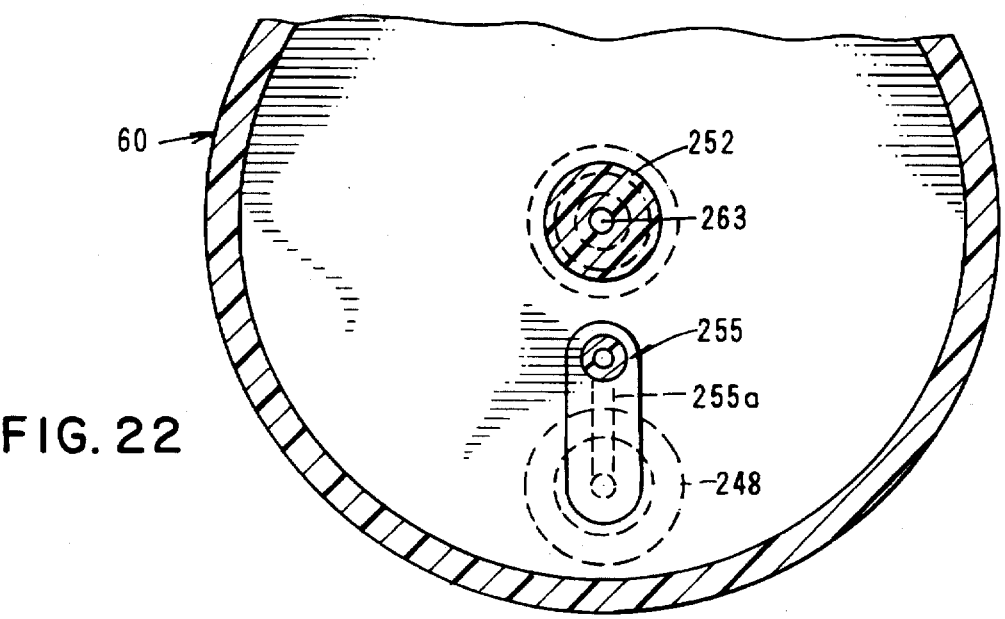
FIG. 22 is a cross-sectional view taken along lines 22—22 of FIG. 21.

Turning now to FIGS. 16 through 22, yet another embodiment of the present invention is there illustrated. This embodiment is similar in many respects to the embodiment shown in. FIGS. 1 through 9 and, accordingly like numbers have been used to identify like components. The primary difference between this last form of the invention and that of FIGS. 1 through 9 is the design of the outlet, or forward portion of the dispensing assembly. More particularly, as best seen in FIG. 21, this form of the invention includes alternate fill means for filling the fluid reservoir of the device. This alternate fill means includes a radially offset inlet, part of which includes check valve means for controlling fluid flow toward the reservoir 94 of the device. This check valve means is housed within a chamber 248 formed in the inboard end of a luer like connector 250 which is connected to an end plate 252 and comprises a valve member 254 having a body portion 254a, a neck portion 254b and an intermediate shoulder portion 254c. Chamber 248 communicates via passageway 255a of manifold element 255 (FIGS. 16 and 21) with an inlet passageway 256 which is formed in end wall 260a of support 260 and which, in turn, communicates with reservoir 94 via annular passageway 256a. Central support 160, which is virtually identical to support 64 of the embodiment shown in FIG. 4, is also provided with an end wall portion 260a having formed thereon radially extending passageways 90 and 92 each of which communicates with reservoir 94. As before, the central portion of passageway 92 communicates with a passageway 96, which, in turn, communicates with the flow control means of the invention. As best seen in FIG. 21, an outlet passageway 263 interconnects the flow control means with an outlet luer like connector 265 which forms an integral part of end plate 252. Connector 265 is designed to receive a closure cap 267 which functions to block fluid flow through passageway 263. Similarly, inlet luer connector 250 is designed to lockably mate with a locking fill cap 270. Cap 270 includes circumferentially spaced locking fins 270a which lockably mate with circumferentially spaced fins 270e provided on fitting 250 (FIGS. 16, 17, and 21). With this arrangement, once cap 270 is connected to fitting 250, it will be securely locked in place thereon and sealably close the inlet passageway thereof.

As best seen in FIG. 16, the flow control means of the present form of the invention comprises an assemblage made up of four disc-like wafers which are mounted within a rate control chamber 271 formed in end wall 260 of central support 260. Wafers 272 and 274 of the assemblage comprise porous glass distribution frits while intermediate wafer 276 comprises a filter member and intermediate wafer 278 comprises a rate control member.

Filter member 276 can be constructed from a wide variety of materials, but a material comprising polysulfone sold by Gelman Sciences under the name and style of SUPOR has proven satisfactory for the purpose. Rate control member 278 is preferably constructed from a thin film, polycarbonate material having extremely small flow apertures ablatively drilled by an excimer laser ablation process. Both the orifice size and unit distribution can be closely controlled by this process. However, a number of other materials can also be used to construct this permeable member including metals, ceramics, plastics and glass. The rate control C member can be specifically tailored to accommodate various delivery regimens including low flow and intermediate flow conditions.

The apparatus of this last form of the invention, is used in the same general manner as previously described to fill reservoir 94 either by means of the fill assembly or by means of the fill port or luer like fitting 250. When filling is accomplished using the alternate fill means, fluid is introduced into passageway 256 by exertion of fluid pressure on valve member 254 sufficient to move shoulder 254c away from seat 250a of fitting 250 so that fluid can flow past valve member body 254a, passageway 255a of manifold element 255, and through a plurality of circumferentially spaced channels 280 formed in fitting 250 through chamber 248, into passageway 255a of manifold 255 and then into passageway 256 (FIG. 19). In this instance filling of the reservoir is accomplished by a separate luer type fill fitting (not shown) and a separate fill line (not shown). After the reservoir is filled, the separate fill fitting is removed and replaced by a sealing closure 270 (FIG. 21). Cap 270 includes circumferentially spaced locking fins 270a which lockably mate with circumferentially spaced fins 270-1 provided on fitting 250. With this arrangement, once cap 270 is connected to fitting 250, it will be securely locked in place thereon.

When it is desired to fill or partially fill reservoir 94 using the fill assembly rather than the alternate fill means, the fill assembly is mated with the fluid delivery assembly in the same manner as previously described, herein in connection with the embodiments of FIGS. 1 through 15.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A fluid delivery apparatus comprising:
   (a) a fluid delivery assembly comprising:
      (i) an elongated housing having walls defining an internal chamber, one of said walls having an outlet passageway;
      (ii) a support assembly connected to said housing, said support assembly including:
         a. an elongated body portion having a receiving chamber and an end wall portion having first and second fluid passageways each having an open end; and
         b. a hollow cannula connected to said end wall portion and extending into said receiving chamber, said hollow cannula being in communication with said first fluid passageway formed in said end wall portion of said elongated body; and
      (iii) an elongated tubular shaped elastomeric member connected proximate its ends to said support, said elastomeric member having a central portion disposed within said internal chamber of said housing and overlaying said open ends of said first and second fluid passageways, said central portion of said elastomeric member being distendable by fluid flowing through said first fluid passageway from a first position in proximity with said support to a second position; and
   (b) a fill assembly interconnected with said fluid delivery assembly comprising:
      (i) a container assembly including:
         a. a container having a body portion, a fluid chamber, and first and second open ends;
         b. closure means for sealably closing said first end of said container, said closure means being pierceable by said hollow cannula;
         c. a plunger telescopically movable within said container from a first location proximate said open end to a second spaced apart location to cause fluid flow into said hollow cannula;
      (ii) an adapter assembly receivable within said receiving chamber of said support assembly, said adapter assembly comprising a hollow housing having a first open end for telescopically receiving a part of said body portion of said container of said container assembly and including a second end.

2. An apparatus as defined in claim 1 in which said hollow housing further includes pusher means for engagement with said plunger of said container assembly to move said plunger within said container between first and second locations.

3. An apparatus as defined in claim 1 in which said fill assembly further includes a cover assembly comprising a cover having a first open end for telescopically receiving a part of said body portion of said container of said container assembly and a second end, said cover being removable from said container to expose said closure means.

4. A apparatus as defined in claim 1 in which said fluid delivery assembly further includes flow control means for controlling fluid flow between said second fluid passageway formed in said end wall portion of said support and said outlet passageway of said elongated housing.

5. An apparatus as defined in claim 1 in which said fluid delivery assembly further includes valve means for controlling fluid flow from said hollow cannula toward said first passageway formed in said end wall portion.

6. An apparatus as defined in claim 1 including alternate fill means for introducing fluid into said second passageway formed in said end wall portion.

7. A fluid delivery apparatus comprising:
   (a) a fluid delivery assembly comprising:
      (i) an elongated housing having walls defining an internal chamber, one of said walls having an outlet passageway;
      (ii) a support assembly connected to said housing, said support assembly including:
         a. an elongated body portion having a receiving chamber and an end wall portion having first and second fluid passageways each having an open end; and
         b. a hollow cannula connected to said end wall portion and extending into said receiving chamber, said hollow cannula being in communication with said first fluid passageway formed in said end wall portion of said elongated body; and
      (iii) an elongated tubular shaped elastomeric member connected proximate its ends to said support, said elastomeric member having a central portion disposed within said internal chamber of said housing and overlaying said open ends of said first and second fluid passageways, said central portion of said elastomeric member being distendable by fluid flowing through said first fluid passageway from a first position in proximity with said support to a second position; and
   (b) a fill assembly interconnected with said fluid delivery assembly comprising:
      (i) a container assembly including:
         a. a container having a body portion, a fluid chamber, and first and second open ends;

b. closure means for sealably closing said first end of said container, said closure means comprising a pierceable septum pierceable by said hollow cannula;

c. a plunger telescopically movable within said container from a first location proximate said open end to a second spaced apart location to cause fluid flow into said hollow cannula;

d. pusher means for engagement with said plunger of said container assembly to move said plunger within said container between first and second locations; and (ii) an adapter assembly receivable within said receiving chamber of said support assembly, said adapter assembly comprising a hollow housing having a first open end for telescopically receiving a part of said body portion of said container of said container assembly and including a second end.

8. A apparatus as defined in claim 7 in which said fluid delivery assembly further includes flow control means for controlling fluid flow between said second fluid passageway formed in said end wall portion of said support and said outlet passageway of said elongated housing.

9. An apparatus as defined in claim 8 in which said flow control means include flow rate control means for precisely controlling the rate of flow of fluid through said outlet passageway of said elongated housing.

10. An apparatus as defined in claim 9 in which said flow rate control means comprises a permeable porous member.

11. An apparatus as defined in claim 9 in which said flow rate control means comprises a rate control element having laser drilled apertures therethrough.

12. An apparatus as defined in claim 9 in which said fluid delivery assembly further includes valve means for controlling fluid flow from said hollow cannula toward said first passageway formed in said end wall portion.

13. An apparatus as defined in claim 9 including alternate fill means for introducing fluid into said second passageway formed in said end wall portion.

14. An apparatus as defined in claim 9 in which said container comprises a glass vial.

15. An apparatus as defined in claim 14 in which said closure means comprises a non-corable elastomeric septum and in which said container assembly further includes a clamping ring for crimping engagement with said glass vial to hold said elastomer septum in position.

* * * * *